(12) United States Patent
Nugent et al.

(10) Patent No.: US 8,658,034 B1
(45) Date of Patent: Feb. 25, 2014

(54) MOBILE PHASE PREPARATION DEVICE FOR LIQUID CHROMATOGRAPHY

(75) Inventors: Kerry Nugent, Penn Valley, CA (US); David Kennedy, Loomis, CA (US)

(73) Assignee: Bruker Michrom, Inc., Auburn, CA (US)

( * ) Notice: Subject to any disclaimer, the term of this patent is extended or adjusted under 35 U.S.C. 154(b) by 0 days.

(21) Appl. No.: 13/602,172

(22) Filed: Sep. 2, 2012

(51) Int. Cl.
*B01D 15/08* (2006.01)

(52) U.S. Cl.
USPC .................. 210/198.2; 210/101; 210/656

(58) Field of Classification Search
USPC ............... 210/656, 659, 101, 137, 143, 198.2
See application file for complete search history.

(56) References Cited

U.S. PATENT DOCUMENTS

| | | | | |
|---|---|---|---|---|
| 4,116,046 A | * | 9/1978 | Stein | 73/61.55 |
| 4,364,263 A | * | 12/1982 | Sankoorikal et al. | 73/61.56 |
| 4,448,684 A | * | 5/1984 | Paradis | 210/198.2 |
| 4,478,713 A | * | 10/1984 | Girot et al. | 210/101 |
| 5,091,092 A | * | 2/1992 | Newhouse et al. | 210/635 |
| 5,242,586 A | * | 9/1993 | Ransohoff | 210/198.2 |
| 5,393,434 A | * | 2/1995 | Hutchins et al. | 210/656 |
| 5,397,467 A | * | 3/1995 | Morgan et al. | 210/198.2 |
| 5,468,643 A | * | 11/1995 | Su et al. | 436/161 |
| 5,520,817 A | * | 5/1996 | Anahara | 210/656 |
| 5,607,581 A | * | 3/1997 | Gerner et al. | 210/198.2 |
| 6,780,315 B2 | * | 8/2004 | Richardson et al. | 210/198.2 |
| 6,893,569 B2 | * | 5/2005 | Zelechonok | 210/656 |
| 7,862,716 B2 | * | 1/2011 | Zelechonok et al. | 210/198.2 |
| 2004/0108273 A1 | * | 6/2004 | Richardson et al. | 210/656 |
| 2009/0294363 A1 | * | 12/2009 | Liu | 210/656 |

OTHER PUBLICATIONS

MacNair, J. E., Lewis, K. C. and Jorgenson, J. W., "Ultrahigh Pressure Reversed Phase Liquid Chromatography in Packed Capillary Columns", Analytical Chemistry, v. 69, pp. 983-989 (1997).

* cited by examiner

*Primary Examiner* — Ernest G Therkorn
(74) *Attorney, Agent, or Firm* — Robic, LLP (57) ABSTRACT

A mobile phase delivery device for use with high pressure liquid chromatography includes a manifold having a plurality of inlets, wherein each inlet is fluidly coupled with a solvent source. The manifold further has a mobile phase outlet that outputs a mobile phase, composed of solvent or solvent mixture, onto an analytical line. The device further includes at least one pump for delivering solvent to the manifold, and a fluid branch in the manifold that is located at a point downstream of the plurality of inlets, and is fluidly coupled with at least one of a pressure sensor and a purge valve.

14 Claims, 4 Drawing Sheets

MOBILE PHASE PREPARATION DEVICE FOR LIQUID CHROMATOGRAPHY

BACKGROUND

The invention relates generally to a mobile phase preparation device for use with liquid chromatography, in particular high pressure liquid chromatography (HPLC) or ultra-high pressure liquid chromatography (UHPLC). Basically, liquid chromatography (LC) is a physical method of separation in which the components to be separated are distributed between a mobile phase and a stationary phase, through or along which the mobile phase percolates in a definite direction.

The field of liquid chromatography started with the use of gravity pressure to move liquids through columns packed with a large particle solid phase support, such as with 20 to 50 micrometers average particle size, in order to separate molecules. In the 1970s, high pressure liquid chromatography was introduced to provide better resolution and faster analyses by using pumps to move liquids through columns packed with small particles (three to ten micrometers) at pressures up to 6,000 psi (~$4.1 \times 10^7$ Pascal). Over the past decade, ultra-high pressure liquid chromatography, pioneered by James W. Jorgenson and co-workers in the late 1990s (see, for instance, Anal. Chem. 1997, 69, 983-989), has become very popular, as it provides even higher resolution and throughput, but requires pumps that move liquids through columns packed with very small particles (less than two micrometers) at pressures up to 15,000 psi (~$1.0 \times 10^8$ Pascal) and more. In order to achieve the maximum benefits of UHPLC, instrumentation needed to be redesigned to withstand these higher pressures, but also to minimize system volumes which adversely impact resolution, throughput and reproducibility at UHPLC pressures.

Figure 1:
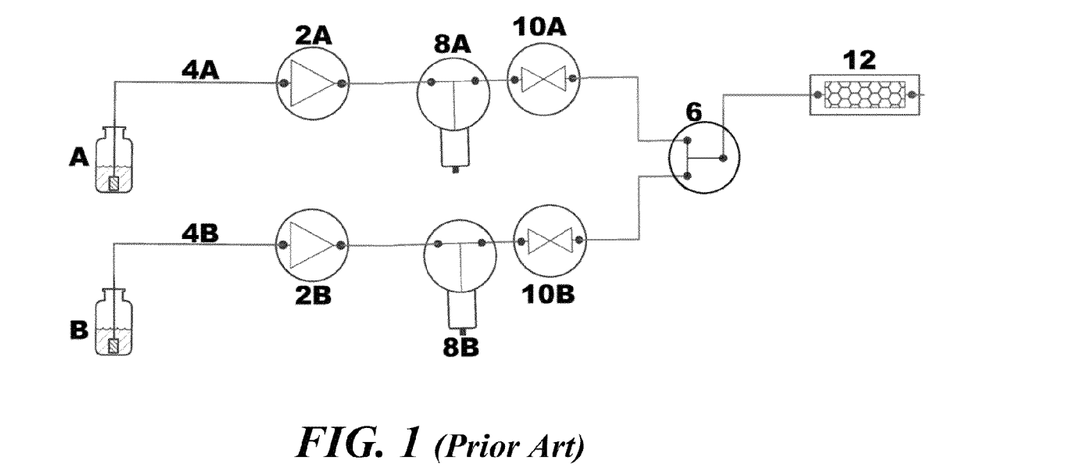
FIG. 1 illustrates schematically a conventional mobile phase preparation device.

Modern commercially available HPLC and UHPLC systems have a pressure transducer and a purge valve in the fluid path of each solvent delivering pump prior to combining the solvents in a manifold (see fluid schematic in FIG. 1). These components, especially the pressure transducer, can add a significant volume to the fluid path between the pump outlet and the manifold inlet, generally between 500 to 1,000 microliters. Although systems can use software to compensate for the compressibility of the different solvents used in each pump, for example by speeding up the pump to compress the solvent, this software compensation gets more difficult to do accurately as the volume of solvent to be compressed increases. At extremes of a gradient separation, characterized by continuous or stepwise change of the composition of the mobile phase during the elution process, such as 0 to 5 percent of one solvent and, correspondingly, 100 to 95 percent of another solvent in a binary system, the solvent from the higher flowing pump can actually flow into the compression region of the lower flowing pump to compress its solvent to the system pressure. This cross flow of solvent can result in inaccurate solvent gradients and/or result in longer re-equilibration times between runs to insure the proper solvent mixture is being proportioned into the mixer at the start of a gradient run.

Although many UHPLC system components have been designed with pre-combination solvent compression in mind, there has not been any previous development that combined multiple system components to properly address these issues.

SUMMARY

In accordance with the principles of the invention, a first embodiment comprises a manifold having a plurality of inlets, wherein each inlet is configured to be fluidly coupled with a solvent source, and further having a mobile phase outlet configured to output a mobile phase, composed of solvent or solvent mixture, onto an analytical line, at least one pump for delivering solvent to the manifold, and a branch located at a point downstream of the plurality of inlets that is fluidly coupled with at least one of a pressure sensor and a purge valve.

Integrating at least one of a pressure sensor and purge valve within a solvent mixing device improves the overall performance of a UHPLC system. By locating at least one of these components at, or downstream of, a point where the solvents combine to form the mobile phase, instead of placing the component before the manifold as known from the prior art, the post pump compression volume can be reduced by a factor of 10 to 100, which greatly reduces system volume and minimizes solvent compressibility issues. Under pressure, solvents undergo compression and this solvent compression, which is different for all solvents and increases as pressure increases, can have a significant impact on the flow rate of the solvents being delivered by UHPLC pumps. By minimizing the volume of solvent to be compressed, the software procedures applied to correct for compressibility, a task generally challenging to implement dynamically as system pressures change during gradient elution UHPLC, can be downscaled, if not dispensed with completely. With systems constructed in accordance with principles of the current invention, the compression volume can be considerably reduced, such as to less than ten microliters, which greatly reduces the impact of solvent compression on the actual flow of the pumps versus the programmed flow.

The analytical line or analytical conduit is generally characterized in that it transmits the mobile phase to be used in a chromatographic run and, to that end, directly or indirectly leads to a chromatographic separation column. On its way there, it passes a point at which liquid sample is introduced into the mobile phase, preferably in a pulse with narrow spatial distribution as to allow for high chromatographic resolution.

The mobile phase may comprise a mixture of a plurality of solvents and is formed generally by combining the different solvents, even if, as a result of the confluence, the distribution of the solvents in the liquid volume of the mixture is not initially homogeneous. Under certain circumstances, however, the mobile phase may also comprise just one solvent, for instance in cases where a gradient elution schedule at some point includes reducing a percentage of one solvent to zero whereas raising the percentage of the other complementary solvent to 100.

In various embodiments, the mobile phase preparation device further comprises a distribution homogenizer fluidly coupled on the analytical line to the mobile phase outlet and being configured to homogenize, as the case may be, an inhomogeneous distribution of solvents in the mobile phase. The distribution homogenizer may comprise a mixer cartridge, for example. Mobile phase preparation devices constructed according to principles of the invention allow the pressure sensor, optionally purge valve and/or distribution homogenizer to be built in close spatial proximity into a single block, such as a solvent mixing device, with customized machining to reduce volumes of each device and eliminate volumes between devices, as well as to reduce the number of ultra-high pressure fluidic connections.

In various embodiments, the at least one pump is a single-piston pump. Preferably, the single-piston pump has a displacement volume of about 15 microliters. One pump can be employed to deliver a plurality of solvents from the solvent sources to the manifold when the total aspiration power generated by the pump is distributed over several different solvent delivery lines. In other embodiments, however, it is also possible to use a plurality of pumps, for example such that each solvent is delivered by an associated pump.

In various embodiments, the pressure sensor is configured to operate up to about 20,000 psi (corresponding to about $1.4 \times 10^8$ Pascal) to facilitate measurements under ultra-high pressure liquid chromatography conditions. Preferably, the purge valve, if present, is fluidly coupled to the pressure sensor downstream thereof.

In various embodiments, the pressure sensor is a pressure transducer. The pressure transducer may comprise a diaphragm sensor that measures fluid displacement. The pressure sensor is fluidly coupled to the flow of mobile phase in a branch off the analytical line and monitors the overall pressure in the mixing device preferably somewhere between a point where the different solvents combine to form the mobile phase, up to a sample injector. If a distribution homogenizer is present, it is preferred to plumb the branch into the analytical line somewhere between the point of confluence and the inlet of the distribution homogenizer as to facilitate a compact and high pressure resistant instrumental configuration.

In various embodiments, the branch includes an outlet at the manifold off the analytical line. In some embodiments, the manifold has two inlets for receiving two solvents to implement a binary gradient elution system, the two inlets and the two outlets being coupled in a cross connection. The cross connection can be a cross fitting. However, this description is not to be construed restrictive. The four arms of the cross connection, or of any other multi-legged manifold, do not have to lie in the same plane. Rather, it is possible to conceive designs of connecting four lines that distinguish from a standard cross fitting.

In various embodiments, the mobile phase preparation device further comprises a controller that operates the at least one pump such that pumping powers for different solvents change over time as to vary a composition of the mobile phase. With such configuration it becomes possible to operate the mobile phase preparation device with gradient elution in order to achieve high flexibility for different analytical investigations.

In various embodiments, the mobile phase preparation device further comprises tubing that fluidly connects an outlet of a pump directly to an inlet of the manifold, wherein a length of the tubing is minimized as to reduce fluid volume between pump and manifold. Consequently, no pressure sensors and/or purge valves, which would add up to the compression volume associated with the respective pump, are located in the solvent delivery line between pump outlet and manifold inlet. In so doing, system performance can be considerably improved.

In various embodiments, the mobile phase preparation device further comprises a controller that acquires pressure measurement data from the pressure sensor and adjusts operation of the at least one pump as a function of the pressure measurement data.

The main achievement of this invention is the reduction of total system volume which improves throughput and overall performance of a UHPLC system. By reducing the volume of the solvents to be compressed at UHPLC pressures prior to combining them to form the mobile phase, the system is able to achieve the desired flows from the pumps much more rapidly, thus resulting in faster equilibration between runs. This lower volume of solvent compression also minimizes any cross contamination between solvents with different compressibility, which improves both the throughput and reproducibility of the UHPLC system for gradient analysis.

In some embodiments, the mobile phase preparation device further comprises a mechanism by which a number of high pressure resistant fluidic connections on fluid lines is minimized. A preferred way of realizing such mechanism is incorporating the manifold, the pressure sensor, optionally the purge valve, as the case may be the distribution homogenizer, a portion of the analytical line, and generally the associated fluid lines in close spatial proximity into a single block of pressure resistant material. Thus, the total number of connections required to integrate pressure sensors and/or purge valves into a UHPLC system can be reduced, which minimizes the opportunity for solvent leaks at high pressures, improving the overall reliability of the UHPLC system. Visual inspection of these high pressure connections and direct access to them for tightening as required is also possible, with no opportunity for solvent leaks to go undetected or to allow solvents to leak into the electronics of the UHPLC system.

In a second aspect, the invention pertains to a method of operating a mobile phase preparation device during a run of high pressure liquid chromatography, comprising the steps: (i) pumping a solvent from a solvent source to an inlet of a manifold; (ii) passing the solvent through a confluence region within the manifold where the solvent can be combined with at least one other solvent, being delivered to the manifold through a different line and inlet, to form a mobile phase; (iii) outputting the resultant mobile phase from the manifold onto an analytical line; and (iv) branching off a portion from the flow of mobile phase at, or downstream from, the confluence region in order to perform at least one of a pressure measurement and venting to exhaust.

In various embodiments, a result of the pressure measurement is used to control the pumping.

In various embodiments, in a binary, tertiary, or quaternary mode of operation, a first solvent is combined with one, two, and three other solvents, respectively, to form the mobile phase.

In a third aspect the invention relates to a solvent mixing device for use with high pressure liquid chromatography, comprising a manifold having a plurality of inlets, wherein each inlet is configured to be fluidly coupled with a solvent source, and further having a mobile phase outlet configured to output a mobile phase, composed of solvent or solvent mixture, onto an analytical conduit, and a dead-ended conduit being plumbed in at a point downstream from the plurality of inlets, and being fluidly coupled with at least one of a pressure sensor and a purge valve.

In various embodiments, the solvent mixing device further comprises a block of high pressure resistant material, such as stainless steel or titanium, into which at least the manifold, the dead-ended conduit, a portion of the analytical conduit, at least one of the pressure sensor and purge valve, and corresponding fluid lines are incorporated, such that high pressure resistant fluidic connections at coupling points of fluid lines are dispensable. The only high pressure resistant fluidic connections that remain are those where the block is fluidly coupled to the outside, such as at the manifold inlets and at the analytical line outlet, or as the case may be at a homogenizer outlet.

In some embodiments, the solvent mixing device further comprises a distribution homogenizer with its fluid lines being incorporated into the block, and being plumbed in to the portion of the analytical conduit.

Preferably, the solvent mixing device comprising a single block of high pressure resistant material has the configuration of a module and can be easily disassembled from, and reinserted into, a mobile phase preparation device, for example, for maintenance and/or cleaning purposes.

BRIEF DESCRIPTION OF THE DRAWINGS

The invention can be better understood by referring to the following figures. The elements in the figures are not necessarily to scale, emphasis instead being placed upon illustrating the principles of the invention (often schematically). In the figures, like reference numerals generally designate corresponding parts throughout the different views.

DETAILED DESCRIPTION

While the invention has been shown and described with reference to a number of embodiments thereof, it will be recognized by those skilled in the art that various changes in form and detail may be made herein without departing from the spirit and scope of the invention as defined by the appended claims.

FIG. 1 shows a fluid schematic of a binary mobile phase preparation device, that is, with input of two solvents A and B, constructed in accordance with the prior art. Each reservoir is fluidly coupled to a pump 2A,B each of which is configured and controlled to deliver solvent from the corresponding reservoir on a solvent delivery line 4A,B to a mixing device 6. The components the solvent further passes online will now be explained in the following in more detail.

Pressure transducers 8A,B monitor the pressure generated at each pump outlet. In addition to monitoring the operation of the pumps 2A,B, the pressure output of the transducer 8A,B usually is tied into the pump flow to provide feedback to the pump 2A,B and insure pressures are in the correct range. This component typically uses a diaphragm sensor that measures fluid displacement, and therefore the volume of this device usually changes with changing pressures. Some HPLC and UHPLC systems utilize a pulse dampener (not shown) in addition to the pressure transducer. In other implementations, the pressure transducer 8A,B itself can also serve as a pulse dampener, minimizing short term pressure fluctuations due to the large volume and compression of the diaphragm. The pressure transducer 8A,B generally is the largest volume of any of the components between pump outlet and manifold inlet. As there is a separate pressure transducer 8A,B for each pump 2A,B, each of these adds its inherent volume to the fluid path of each pump 2A,B so that a large volume results and this volume must be compressed before the correct flow for each pump 2A,B can be realized.

Each of the pressure transducers 8A,B is fluidly coupled to a purge valve 10A,B downstream. These purge valves 10A,B allow the pumps 2A,B to be primed and to rapidly change solvents in each pump 2A,B as required. In lab practice, this is usually done once a day. The volume of the purge valve 10A,B typically is not as large as the volume of the pressure transducer 8A,B, but still perceptibly contributes to the overall fluid volume between pump outlet and manifold inlet. Furthermore, the valve 10A,B requires two additional high pressure connections between pump outlet and manifold. These high pressure connections are potentially weak spots in a highly pressurized system, the failure of which could pose a threat to surrounding instrumentation and lab personnel.

The Tee fitting 6 combines the flows from the two pumps 2A,B prior to a mixer cartridge 12. During operation, the mixer cartridge 12 homogenizes efficiently, as the case may be, any inhomogeneously distributed solvents in the mobile phase to insure a smooth baseline and retention time reproducibility for different chromatographic runs. Several different mixer designs are available on the market, depending mainly on the pumps and associated volumes, and are therefore known to one of ordinary skill in the art.

From the mixer cartridge 12 the homogenized mobile phase, after passing an injector module (not shown) for injecting sample into the mobile phase stream, is usually delivered to the inlet of a column (not shown) where chromatographic separation takes place, and from there on to a detector (not shown).

Figure 2:
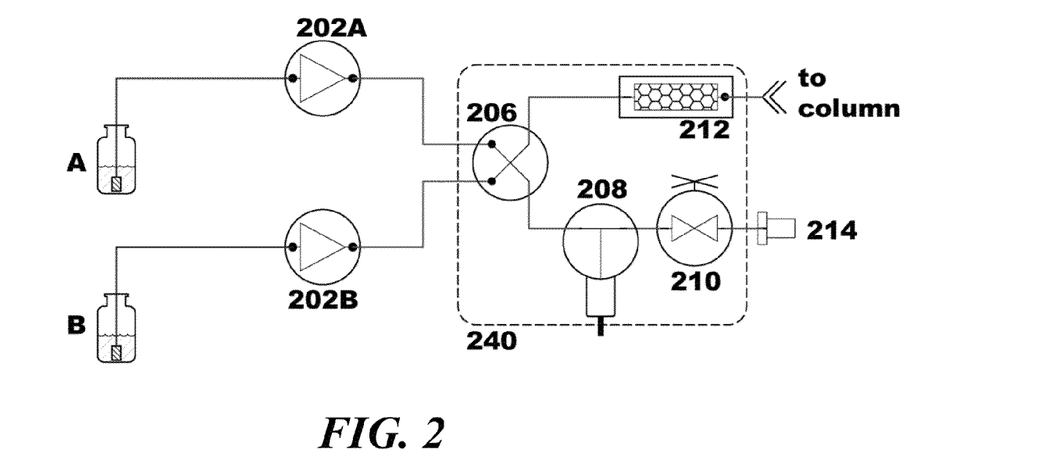
FIG. 2 illustrates schematically a mobile phase preparation device according to principles of the present invention.

FIG. 2 shows a first embodiment of a binary mobile phase preparation device according to principles of the present invention in a fluid schematic view. As can be seen, the outlets of the pumps 202A,B are directly fluidly connected to the respective inlet of cross connection 206 without any intermediate components, such as pressure transducers and/or purge valves, which would increase the system volume between pumps 202A,B and cross 206 and give rise to afore-discussed compressibility issues. Instead, the present embodiment comprises only one pressure transducer 208 plumbed in offline (in the sense of 'off the analytical line') to the flow from each pump 202A,B to mixer cartridge 212, so its volume does not add up to the compression volume of each pump 202A,B. Preferably, the pressure readings of the pressure transducer 208 are used by a controller to adjust operation of the pumps 202A,B. Due to the reduced compression volume between each pump 202A,B and cross 206 the software correction for different solvent compressibility is less important and can be implemented in a less complex manner.

Moreover, the present embodiment has a single purge valve 210, again plumbed in offline to the flow from the pump outlets to the mixer cartridge 212. One outlet of the single purge valve 210 is closed as indicated by the cross. In principle, it provides the same function as individual purge valves, such as purging and venting to exhaust, but without the extra volume and additional high pressure fittings on the solvent delivery line between pumps 202A,B and cross 206.

In the embodiment shown, cross connection 206 replaces the Tee fitting shown in the prior art schematic of FIG. 1. The additional fourth leg of the cross connection 206 is a dead ended line through the pressure transducer 208 to the purge valve 210. This arrangement allows the pressure transducer 208 and purge valve 210 to operate properly within the system, but keeps them out of the fluid streams between the pump outlets and the cross 206. Using this arrangement, it is possible to reduce the volume of fluid to be compressed under high pressures to less than ten microliters. In comparison, in conventional HPLC and UHPLC systems as shown schematically in FIG. 1 this fluid compression volume for each pump can amount to 500 to 1,000 microliters or more.

The mixer cartridge 212 arranged on the analytical line between the mobile phase outlet of the cross connection 206 and a chromatographic column (not shown) preferably is also chosen to have low volume. It should be well suited for flow ranges typically used in analytical LC systems, such as ranging from 100 to 5,000 microliters per minute, and should have good sweep out characteristics. With such characteristics, good performance and throughput of HPLC and UHPLC systems can be achieved.

For the sake of completeness, in the present embodiment, Luer fitting 214 is generally attached to the waste leg of the purge valve 210 (on a low pressure side) to allow the user to attach a syringe to rapidly pull fresh solvents through the pumps 202A,B for priming and solvent changeover. Due to its arrangement offline, however, it does not contribute to the decisive compression volumes of the pumps 202A,B.

Generally, the invention removes large solvent volume components from the solvent stream between the pump outlets and the manifold, for example by plumbing them in to a single manifold at one leg thereof so that only a single pressure transducer and purge valve are plumbed in offline to the mobile phase flows as depicted in FIG. 2. Although these components, now located downstream compared to their prior art counterparts, also have significant volumes, they are compressed by the total solvent flow from the pumps and there is no cross flow between the two or several solvent streams prior to the mixer cartridge. This results in very accurate solvent compositions and rapid system re-equilibration, allowing high throughput and reproducible gradient separations independent of the relative solvent flows and system pressures.

In a particularly favorable embodiment, the cross connection 206, the pressure transducer 208, optionally the purge valve 210, and the mixer cartridge 212 together with fluid lines are incorporated into a block of high pressure resistant material (indicated by the dashed contour 240) in close spatial proximity to form a solvent mixing device, such that high pressure resistant fluidic connections at the fluid couplings of these components can be dispensed with. The block may be made from stainless steel or titanium, for example.

Compared to prior art designs as represented by the fluid schematic of FIG. 1, the mobile phase preparation device requires a lower total number of high pressure resistant fluidic connections (represented by bold black dots). In the embodiment of FIG. 2 it is seven connections (two at pump inlets, two at pump outlets, two at manifold inlets, and one at mixer cartridge outlet) whereas the prior art design shown in FIG. 1 requires seventeen (two at pump inlets, two at pump outlets, four at transducers, four at purge valves, three at Tee connection and two at mixer cartridge). In so doing, a risk of potential leaks that could adversely impact system performance and pose danger for the surrounding instrumentation as well as lab personnel is reduced. It goes without saying that the number of fluidic connections would also be reduced even if the afore-mentioned components, constituting an exemplary solvent mixing device, were not incorporated into a single block. Then, however, the reduction would be less pronounced from seventeen to fourteen (when comparing FIGS. 1 and 2).

The reduced solvent compression referred to above especially improves gradient elution systems using two or more pumps to deliver two or more different solvents. Albeit the principles of the present invention can also be employed with mobile phase separation devices that use only one pump to deliver a plurality of solvents. In gradient elution, large solvent compression volumes can result in cross flow of one solvent into the post pump volume of the other solvent, resulting in significant changes to the solvent composition versus what was programmed. This is especially true at extremes of the solvent gradient, where one pump is running at significantly higher flow rates than the other pump(s). This problem that usually manifests itself in impaired reproducibility of the retention time of sample compounds and/or in longer re-equilibration times required to insure good performance can be overcome by methods and devices configured in accordance with principles of the present invention.

Figure 3A:
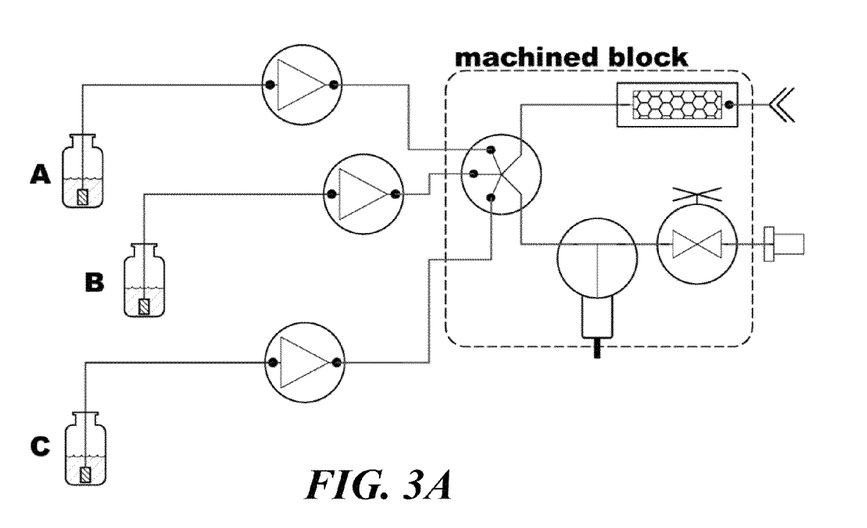
FIGS. 3A-B illustrate schematically mobile phase preparation devices according to principles of the present invention with tertiary and quaternary configurations, respectively.
Figure 3B:
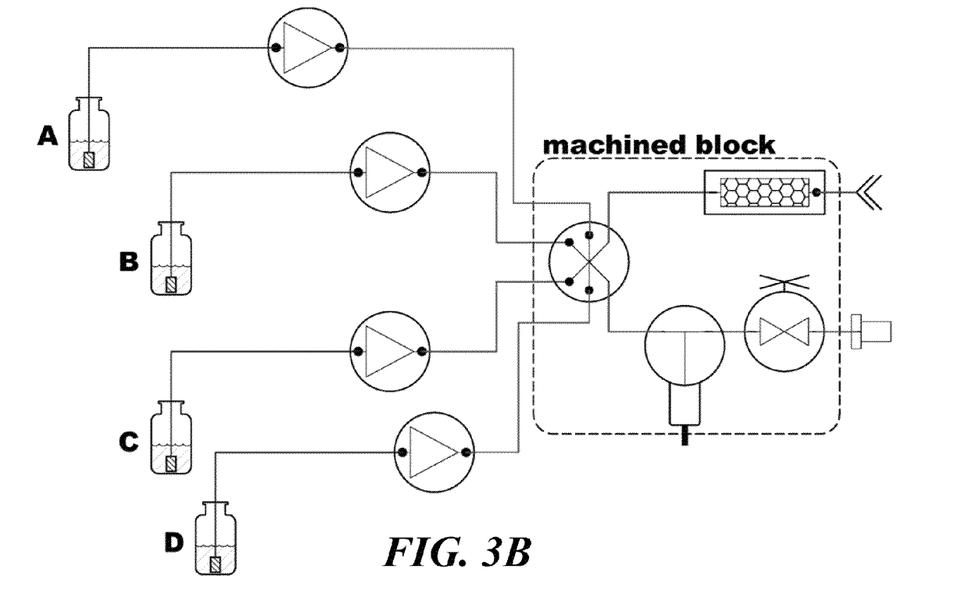

FIGS. 3A-B show embodiments of the present invention where more than two solvents are delivered to a solvent mixing device in order to constitute a mobile phase for liquid chromatography. With three solvents A,B,C involved (FIG. 3A) the system is tertiary. With four solvents A,B,C,D involved (FIG. 3B) the system is quaternary. As regards the other components of the mobile phase preparation device the same configurations can be employed. It is understood that the manifold has to be slightly adapted to be able to receive more than two streams of solvent, for example, resembling a hub with several spikes. It goes further without saying that the number of solvents to be combined is in principle not limited to four. Systems exceeding that number are also conceivable and can be readily implemented by one of ordinary skill in the art when being aware of the present disclosure.

Figure 4:
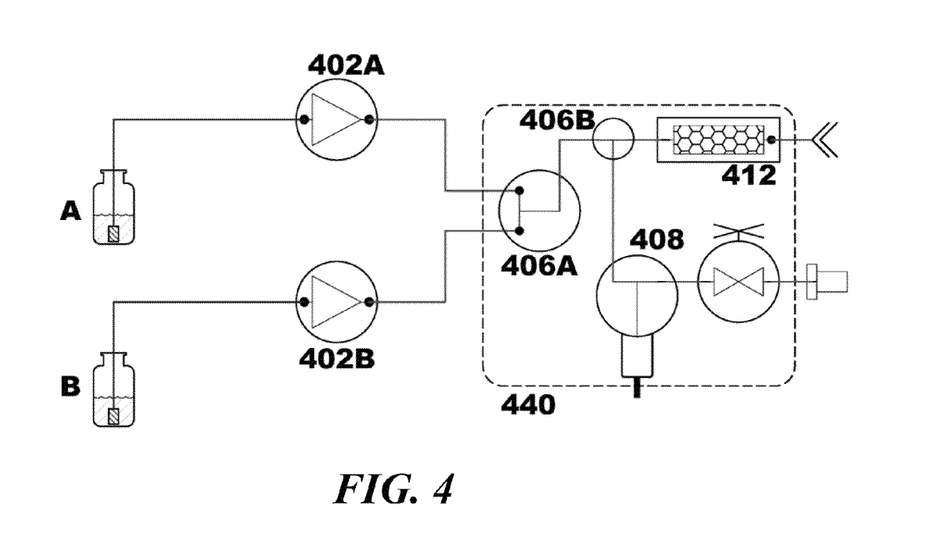
FIG. 4 illustrates another embodiment of a binary mobile phase preparation device according to principles of the invention.

FIG. 4 shows another fluid schematic of an embodiment of a binary mobile phase preparation device according to principles of the invention. In contrast to the embodiment shown in FIG. 2, the present implementation comprises two Tee connections 406A,B. The first Tee connection 406A has two inlets for receiving flows of the two solvents A,B delivered by pumps 402A,B, and one mobile phase outlet for outputting the mobile phase, resulting from the confluence of the two solvents A,B, onto the analytical line. Instead of providing a branch in the confluence region of the solvents A,B, it is implemented further downstream in the second Tee connection 406B. The second Tee connection 406B has one inlet for receiving the mobile phase output from the first Tee connection 406A, one outlet for transmitting the mobile phase to the subsequent mixer cartridge 412, and another outlet off the analytical line that is fluidly coupled to the inlet of single pressure transducer 408 and leads onto a line which is in principle dead-ended. An advantage of this exemplary implementation is that retrofitting a set-up as shown in the prior art schematic of FIG. 1 to comply with the principles of the present invention is easier, since the Tee connection 6 for combining the solvents A,B can remain in the device while the pressure transducers 8A,B and purge valves 10A,B have to be removed and another Tee connection 406B has to be plumbed in between the first Tee 406A and the mixer cartridge 412.

If the two Tee connections 406A,B, the pressure transducer, optionally the purge valve, and the mixer cartridge together with the respective fluid lines are incorporated into a single block 440 so that high pressure resistant fluidic connections within the block are dispensable, the total number of high pressure resistant fluidic connections results in seven, actually the same number found with the implementation shown in FIG. 2. If no block design is foreseen, the total number will still be reduced, however, just by the smallest number of one fluidic connection compared to the configuration shown in FIG. 1.

Figure 5:
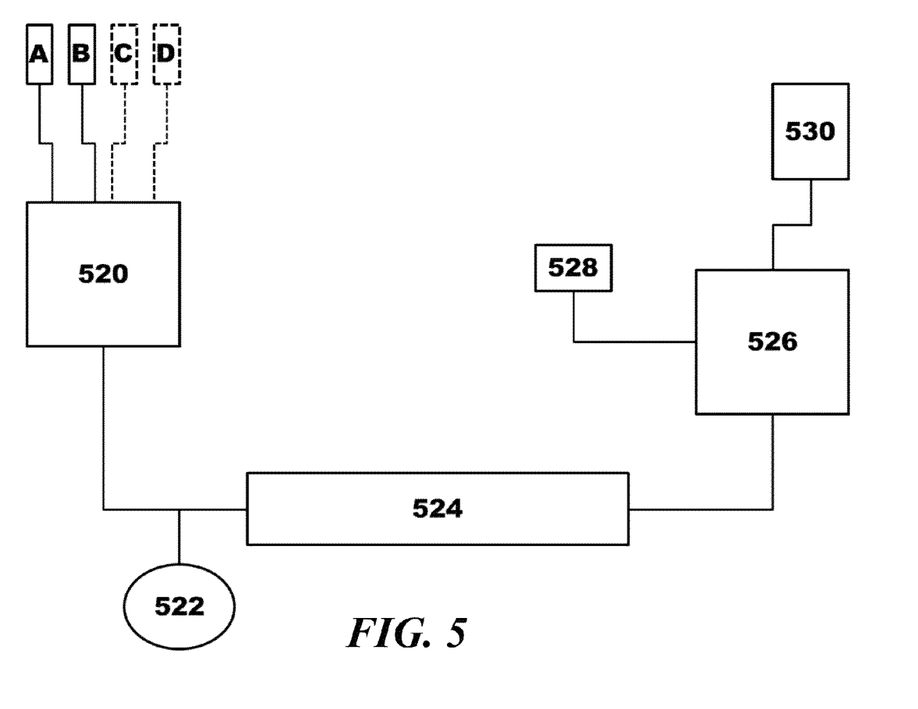
FIG. 5 shows schematically a liquid chromatography set-up which may incorporate a mobile phase preparation device according to principles of the invention.

FIG. 5 shows a schematic of a high pressure liquid chromatography separation device where a mobile phase preparation device, and/or a solvent mixing device, according to principles of the invention can be employed.

Solvents A,B (C,D) are provided in appropriate reservoirs, such as glass containers which can be tapped through the cap via flexible tubes to allow for quick and easy replacement thereof. If two solvents A,B are combined to form a mobile phase, a binary gradient elution system can be operated. If more solvents C,D (indicated by the dashed contours) are needed, tertiary and quaternary systems can be implemented, respectively. A degasser (not shown) may be plumbed in to the solvent delivery lines in order to remove possible bubbles from the solvent streams, which, if present, could impair proper formation of a mobile phase with well-defined solvent ratios.

A mobile phase preparation device 520 is connected to the plurality of solvent sources and is responsible for delivering solvents A,B (C,D) to a mixer, combining them, homogenizing, as the case may be, an inhomogeneous distribution of solvents A,B (C,D) in the freshly formed mobile phase, and outputting the resultant homogeneous mobile phase onto an analytical line. Downstream of the mobile phase preparation device 520, high pressure is imposed on the mobile phase in order to drive it through the densely packed analytical column arranged further downstream. The mobile phase preparation device 520 can be implemented in accordance with the principles of the present invention, and as described in conjunction with specific embodiments illustrated in the previous figures. In particular, it may comprise a solvent mixing device as hereinbefore described. Typical flow rates of mobile phase as it exits the mobile phase preparation device 520 on the analytical line are on the order of milliliters per minute.

Downstream from the outlet of the mobile phase preparation device 520 an injector 522 is located, through which a liquid sample is injected into the continuously flowing mobile phase stream. Once injected, the mobile phase carries the sample into the LC column 524. The column 524 contains the chromatographic packing material needed to effect the separation as is generally known in the art.

Furthermore, a detector 526 is coupled to the outlet side of the column 524 in order to detect the separated compound bands as they elute therefrom. Possible implementations of detectors 526 include, for instance, UV absorbance detectors, fluorescence detectors and evaporative light scattering detectors. It is also possible to input the eluate of the LC into a mass spectrometer to analyze the compounds separated by liquid chromatography, for example via a spray ionization source which transfers analytes of interest from the liquid phase into the gas phase required for mass spectrometry. In some cases, it may further be useful to couple multiple detectors in series or in parallel. For example, a UV absorbance detector can be used in combination with a mass spectrometer. In so doing, an injected sample can be investigated in two different ways and thus more thoroughly than with only one of the afore-mentioned detection methods alone.

After the detection process, the residual mobile phase exits the detector 526 and can be sent to waste 528 or collected, for example to be cleaned and reconditioned, or collected as separated samples for further analysis. In principle, all components in the solvent delivery lines, analytical line and dead-ended line, used for pressure measurement and purging, have to be equipped and connected with high pressure resistant conduits and high pressure resistant fittings to reliably withstand the high pressure load exerted thereon during operation.

Normally, the detector 526 communicates with a computer 530 that records the signal output therefrom and converts it into chromatograms, which in turn can be displayed on a screen or kept accessible for further examination, such as for identifying and quantifying the concentration of the sample constituents.

Figure 6:
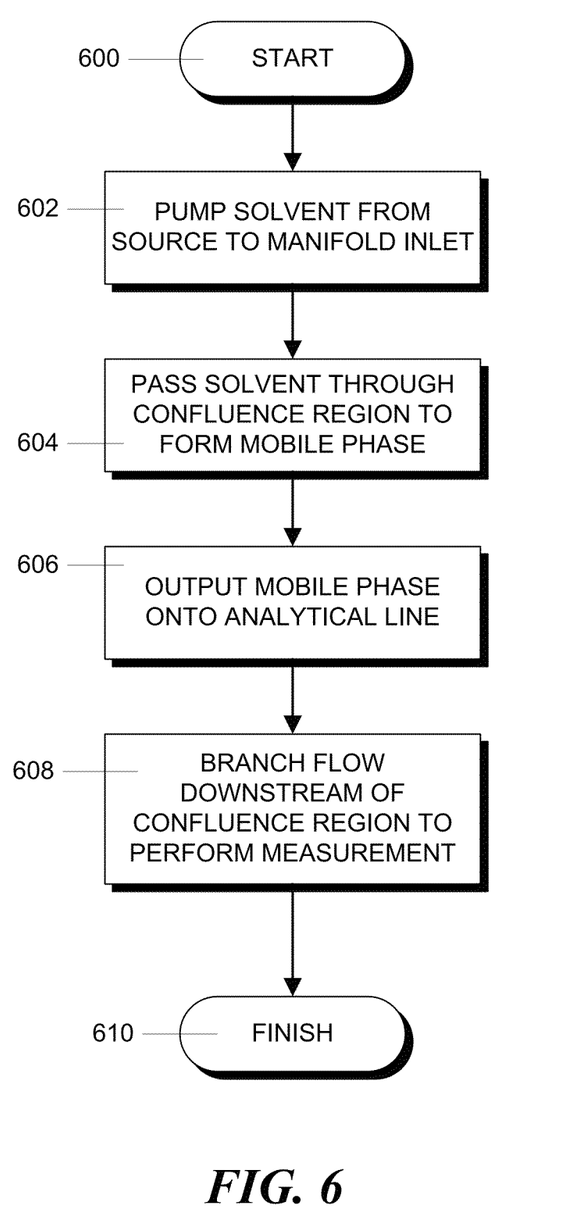
FIG. 6 shows the steps in an illustrative method for operating a liquid chromatography system in accordance with the principles of the invention.

A method of operating a mobile phase preparation device during a run of high pressure liquid chromatography is shown in FIG. 6. The method starts in step 600 and proceeds to step 602 where a solvent is pumped from a solvent source to an inlet of a manifold. Next, in step 604 the solvent is passed through a confluence region within the manifold where the solvent can be combined with at least one other solvent, being delivered to the manifold through a different line and inlet, to form a mobile phase. Then, in step 606, the resultant mobile phase is output from the manifold onto an analytical line. In step 608, a portion from the flow of mobile phase is branched off at, or downstream from, the confluence region in order to perform at least one of a pressure measurement and venting to exhaust. The method then finishes in step 610.

The above description has been focused on applications under ultra-high pressure conditions, that is, at about 6,000 psi (~4.1×10$^7$ Pascal) and more. However, it goes without saying that the beneficial effects brought about by the invention, such as reduced pump compression volume and, as the case may be, reduced number of high pressure resistant fluidic connections, may also prove valuable in lower pressure regimes which are generally considered part of high pressure liquid chromatography. Furthermore, future applications may exceed the ultra-high pressure limits typically observed in today's ultra-high pressure liquid chromatography. The present disclosure is therefore not to be construed restrictive in this regard.

It will be understood that various aspects or details of the invention may be changed, or various aspects or details of different embodiments may be arbitrarily combined, if practicable, without departing from the scope of the invention. Generally, the foregoing description is for the purpose of illustration only, and not for the purpose of limiting the invention which is defined solely by the appended claims.

What is claimed is:

1. A mobile phase preparation device for use with a high pressure liquid chromatography system, comprising:
   a manifold having a plurality of inlets, each inlet fluidly coupled with a solvent source, and the inlets being fluidly coupled to a mobile phase outlet that outputs a mobile phase, composed of at least one solvent, onto an analytical line;
   at least one pump for delivering solvent to the manifold; and
   a manifold branch that is located at a point downstream of the plurality of inlets and is fluidly coupled with at least one of a pressure sensor and a purge valve.

2. The device of claim 1, further comprising a distribution homogenizer that is fluidly coupled to the analytical line at the mobile phase outlet and homogenizes an inhomogeneous distribution of solvents in the mobile phase.

3. The device of claim 2, wherein the distribution homogenizer comprises a mixer cartridge.

4. The device of claim 1, wherein the at least one pump is a single-piston pump.

5. The device of claim 1, wherein the pressure sensor is configured to operate up to about 20,000 psi (~1.4×10$^8$ Pascal).

6. The device of claim 1, wherein the purge valve is fluidly coupled to the pressure sensor.

7. The device of claim 1, wherein the pressure sensor is a pressure transducer.

8. The device of claim 7, wherein the pressure transducer comprises a diaphragm sensor that measures fluid displacement.

9. The device of claim 1, wherein the branch includes a first outlet connected to the mobile phase output and a second outlet.

10. The device of claim 9, wherein the manifold has two inlets for receiving two solvents, the two inlets and the first and second outlets being coupled to each other in a cross connection.

11. The device of claim 1, further comprising a controller that operates the at least one pump such that pumping powers for different solvents change over time as to vary a composition of the mobile phase.

12. The device of claim 1, further comprising tubing that fluidly connects an outlet of the at least one pump directly to an inlet of the manifold, wherein dimensions of the tubing are minimized as to reduce fluid volume between pump and manifold.

13. The device of claim 1, further comprising a controller that acquires pressure measurement data from the pressure sensor and adjusts operation of the at least one pump as a function of the pressure measurement data.

14. The device of claim 1, wherein the manifold is constructed as a machined block of material in order to minimize high pressure resistant fluidic connections on fluid lines.

* * * * *